(12) United States Patent
Setala

(10) Patent No.: US 7,494,277 B2
(45) Date of Patent: Feb. 24, 2009

(54) METHOD AND APPARATUS FOR MEDICAL X-RADIOGRAPHY

(75) Inventor: Henri Setala, Littoinen (FI)

(73) Assignee: PaloDEx Group Oy (FI)

( * ) Notice: Subject to any disclaimer, the term of this patent is extended or adjusted under 35 U.S.C. 154(b) by 112 days.

(21) Appl. No.: 11/753,939

(22) Filed: May 25, 2007

(65) Prior Publication Data

US 2007/0280422 A1 Dec. 6, 2007

(30) Foreign Application Priority Data

May 31, 2006 (FI) .................................. 20060532

(51) Int. Cl.
*G01D 18/00* (2006.01)
(52) U.S. Cl. ....................... 378/207; 378/163
(58) Field of Classification Search ................ 378/163, 378/205, 207, 38–39
See application file for complete search history.

(56) References Cited

U.S. PATENT DOCUMENTS

| | | | |
|---|---|---|---|
| 6,243,439 B1 | 6/2001 | Arai et al. | |
| 6,990,174 B2 | 1/2006 | Eskelinen | |
| 7,097,357 B2 * | 8/2006 | Johnson et al. | 378/205 |
| 2005/0129296 A1 | 6/2005 | Setala | |
| 2007/0280422 A1 * | 12/2007 | Setala | 378/163 |

* cited by examiner

*Primary Examiner*—Hoon Song
(74) *Attorney, Agent, or Firm*—Andrus, Sceales, Starke & Sawall, LLP

(57) ABSTRACT

The invention relates to a method for eliminating error elements caused by movements of an imaged object in X-radiography, said method comprising performing X-radiography on an imaged object for compiling three-dimensional X-radiographic information. The method comprises creating a model geometry of an X-ray imaging process, said creation work comprising a determination of the location for two or more position markers in a set of coordinates graded for an X-ray imaging apparatus. When X-radiography of an imaged object is completed, predictions are worked out regarding the locations of position markers during the imaging session. The locations and predictions determined on the basis of the model geometry are used as a basis for defining projected or most likely locations for the position markers and an automatic position markers identification method is applied for finding the locations of position markers from within a search area in the X-radiographic information. When the locations of at least two position markers have been found with the automatic position markers identification method, a minimization of offsets between the projected locations of position markers and the locations of position markers looked up by the automatic identification method is performed by searching for a minimum point of the function for eliminating the error elements resulting from movements of an imaged object.

16 Claims, 2 Drawing Sheets

METHOD AND APPARATUS FOR MEDICAL X-RADIOGRAPHY

FIELD OF THE INVENTION

The objective in medical X-radiography is to provide images of an object as high quality as possible from the standpoint of a diagnostic effort.

BACKGROUND OF THE INVENTION

In order to enable creating a three-dimensional model of an object by X-radiography, the object must be radiographed from more than one direction. However, the creation of a sufficiently precise three-dimensional model in medical X-radiography requires that imaging be effected from a plurality of directions and effective calculation algorithms be utilized. In medical X-radiography, it is a human being that constitutes the imaged object and, hence, the imaged object shall be subsequently referred to as a patient.

One of the most serious sources of error in three-dimensional medical X-radiography results from movements of a patient during the imaging session. This source of error, even if an X-ray image may not be totally ruined thereby, results in X-ray images which are more blurred, thereby leading to uncertain interpretations and, in a worst case scenario, to false diagnoses.

In prior art, a solution to this problem element has been pursued as described in U.S. Pat. No. 6,243,439 "CT scanning apparatus", whereby information acquired by means of a position marker is utilized in such a way that, as a position marker is radiographed from all directions, the orbit of said position marker can be provided with a sine curve which enables images picked up from various directions to coincide with each other.

A notable drawback in this prior art solution is that in medical applications of X-radiography, wherein the object is imaged from within a limited angle and the number of captured X-ray images is limited, there is no way of even considering that type of solution which is based on a sine curve in the orbit.

BRIEF DESCRIPTION OF THE INVENTION

An objective of the invention is to achieve to a significant degree the elimination of error elements caused by patient movements. This is accomplished by a proposed method of the invention for eliminating error elements resulting from movements of an object in X-radiography, said method comprising performing X-radiography on an imaged object for compiling three-dimensional X-radiographic information. The method comprises creating a model geometry of an X-ray imaging process, said creation work comprising a determination of the location for two or more position markers in a set of coordinates graded for an X-ray imaging apparatus. When X-radiography of an imaged object is completed, predictions are worked out regarding the locations of position markers during the imaging session. The locations and predictions determined on the basis of the model geometry are used as a basis for defining projected or most likely locations for the position markers and an automatic position markers identification method is applied for finding the locations of position markers from within a search area in the X-radiographic information. When the locations of at least two position markers have been found with the automatic position markers identification method, a minimization of offsets between the projected locations of position markers and the locations of position markers looked up by the automatic identification method is performed by searching with an optimization method for the minimum point of a penalty function for eliminating the error elements resulting from movements of an imaged object.

The invention relates also to an X-ray imaging apparatus for eliminating error elements resulting from movements of an imaged object in X-radiography, comprising imaging means for performing X-radiography on an imaged object for compiling three-dimensional X-radiographic information. The X-ray imaging apparatus comprises means for creating a model geometry of an X-ray imaging process, said creation work comprising a determination of the location for two or more position markers in a set of coordinates graded for the X-ray imaging apparatus, means for working out predictions regarding the locations of position markers during X-radiography, and means for defining projected or most likely locations for position markers on the basis of determined locations and predictions based on the model geometry. The X-ray imaging apparatus comprises means for applying an automatic position markers identification method for finding the locations of position markers from within a search area in the X-radiographic information, and means for eliminating the error elements resulting from movements of an imaged object, such that when the locations of at least two position markers have been found with the automatic position markers identification method, a minimization of offsets between the projected locations of position markers and the locations of position markers looked up by the automatic identification method is performed by searching with an optimization method for the minimum point of a penalty function.

A basis of the invention is that the method comprises creating a model geometry of an X-ray imaging process, said creation work comprising a determination of the location for two or more position markers in a set of coordinates graded for an X-ray imaging apparatus. When X-radiography is completed, predictions are worked out regarding the locations of position markers during the imaging session. The locations and predictions determined on the basis of the model geometry are used as a basis for defining projected or most likely locations for the position markers. When the locations of at least two position markers have been found with an automatic position markers identification method (e.g. US2005129296, H. Setälä), a minimization of offsets between the projected locations of position markers and the locations of position markers looked up by the automatic identification method is performed by searching with an optimization method for the minimum point of a penalty function for eliminating the error elements resulting from movements of an imaged object.

By virtue of the invention, a possibility is provided of eliminating error elements caused by patient movements in medical X-radiography, wherein the imaging angle is limited and/or the number of images captured from a patient is limited, for example at the steps of 5-degree imaging angle.

LIST OF FIGURES

DETAILED DESCRIPTION OF THE INVENTION

Embodiments of the invention are most conveniently used in medical X-radiography, wherein a patient is not totally exposed to radiation from every direction, since the amount of radiation received by the patient must be minimized or since there is no actual reason to irradiate the patient except from within a limited angle. The imaging performed by means of a panoramic imaging apparatus in dental X-radiography is a good example of medical X-ray imaging with no need to irradiate a patient except from within a limited angle in order to enable capturing necessary images of the patient's denture or elsewhere from the head and neck area.

Figure 1:
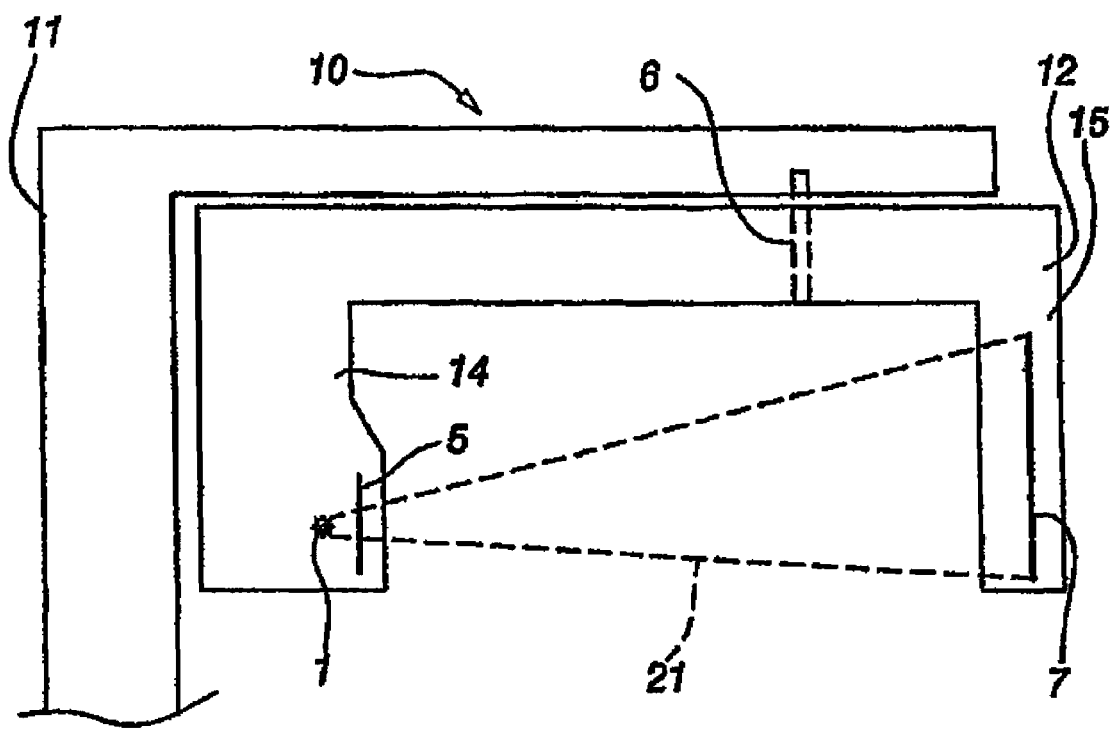
FIG. 1 shows a medical X-ray imaging apparatus by way of example.

Referring to FIG. 1, there is shown an exemplary view of a panoramic dental imaging apparatus, enabling the compilation of three-dimensional X-radiographic information about an imaged object. A panoramic imaging apparatus 10 shown in FIG. 1 includes a vertical member 11 from which extends a horizontal member 10, in support of which is suspended a C-frame 12 rotatably about a pivoted axle 6, one vertical leg 14 thereof being provided with an X-ray source having its focus indicated by reference numeral 1 and a primary collimator present in its vicinity being indicated by reference numeral 6. The other vertical leg 15 is provided with a slit camera, comprising a detector 7 such as, for example, a CCD detector.

In panoramic imaging, the object to be imaged is set between the C-frame's 12 leg members by means of appropriate guides and supports, followed by activating the X-ray source and rotating the C-frame around the pivoted axle 6, the primary collimator 5 having its aperture selected such that a beam 7 present in a substantially vertical plane is directed towards the object in line with the substantially vertically extending slit of a slit camera mounted on the C-frame's 12 leg member 15. After transmission through the object, the radiation lands through said slit on the slit camera's detector 7, from which the image information put together from the received radiation is conveyed to a computer, typically by way of image processing electronics.

The three-dimensional X-radiographic information is compiled with the apparatus of FIG. 1 in such a way that an object to be imaged is radiographed for 2D projection images from within a limited, for example 50 degrees wide angle. After this, the two-dimensional X-radiographic information presently in the form of projection images is processed computationally by a computer for constructing three-dimensional X-radiographic information about the imaged object. U.S. Pat. No. 6,990,174 (J. Eskelinen) describes in more detail the way of using a panoramic imaging apparatus for capturing projection images from an object to be imaged. This type of 3D reconstructive computation requires that the geometry of 2D projection images used as input data for calculation be known exactly in relation to a patient.

Preferred embodiments of the invention involve procedures, on the basis of which it will be possible to eliminate, even in an automated manner, error elements caused by movement of an imaged object in medical X-radiography. The imaging area is provided with position markers which are in permanent contact with respect to an imaged object or patient. Thus, the position markers move whenever the patient moves.

An X-ray imaging process is worked up for a model geometry for each type of apparatus, or even each set of equipment, by imaging a specimen that comprises two or more, for example 30 position markers, at the exact locations designated therefor. In one or more two-dimensional images, the model geometry simulates the locations of position markers present in a three-dimensional set of coordinates. After the actual imaging of a patient, including position markers within the imaging area, has been completed, predictions regarding the locations and/or attitudes (relative to each other) of the position markers are worked out without making use of said model geometry. The locations and predictions determined on the basis of a model geometry shall constitute a basis for determining projected or most likely locations for position markers.

When the projected locations for position markers are determined, a preferred embodiment of the invention comprises selecting the order considered to be most favorable of searching position markers and the shape of a search area considered to be most favorable. The search of position markers from X-radiographic information is performed with an automatic position markers identification method. The position markers automatic identification method may be based for example on a method set forth in the patent application US2005129296 (H. Setälä), wherein the automatic pattern recognition of position markers is based on the calculation of directions for the gradient vectors of intensities. The gradient vectors of intensities are used as a basis for defining from the projection image a search area, in which the gradient vectors of intensities change directions within a previously defined range.

When the location data of more than one position marker has been picked up by the automatic identification method, a minimization of offsets between the projected locations of position markers and the locations of position markers looked up by the automatic identification method is performed by searching for the minimum point of a penalty function for eliminating the error elements resulting from movements of an imaged object.

As the method progresses, it will be possible to apply an optimization method for changing the size of a search area in X-radiographic information, i.e. the area which is searched by the automatic identification method for the locations of position markers. 6. As a first term A(x), the penalty function comprises a root-mean sum of the locations of projected position markers and the locations of position markers determined by the automatic identification method. A second term B(x) of the penalty function is determined to be constituted by offsets between the locations of projected position markers and the locations of position markers determined by the automatic identification method, a root-square sum being calculated therefor for use as a second term of the penalty function. Thus, the second term of a penalty function refers to a "penalty" calculated for the extents of a patient's movements. Since there are differences between the adversities of various directions of movement as regards the technical aspect of imaging, it is possible to computationally penalize certain directions of movement more than others.

When the implementation procedures of the invention have been carried out once, the implementation for a method of the invention will be changed in such a way that there is no more need for predictions made about the locations of position markers without using a model geometry. Namely, the 3D information acquired in the first process cycle about the location of one or more position markers can be utilized in the next process cycle as initial information during the imaging session of an object to be imaged for a 3D set of coordinates (virtually) graded for an X-ray imaging apparatus.

Because there is no way of knowing exactly the location and position in which a patient, and position markers accompanying the patient, move about during an imaging session, the certainty regarding the locations and attitudes of position markers will become more focused as the process cycles of the invention progress and calculations are continued towards the minimum point of a penalty function in order to enable the elimination of error elements caused by patient movements.

Regarding a penalty function useful in an embodiment of the invention, the following is presented as an example:

$$f(x) = \sum_{IMG}\sum_{MRK} |M_{IMG,MRK}(x) - D_{IMG,MRK}|^2 + \sum_{DOF} (W_{DOF}\Delta_{DOF}(x))^2$$

which consists of a verbally defined first term A(x) and a second term B(x).

$$A(x) = \sum_{IMG}\sum_{MRK} |M_{IMG,MRK}(x) - D_{IMG,MRK}|^2$$

$$B(x) = \sum_{DOF} (W_{DOF}\Delta_{DOF}(x))^2$$

The individual formula elements are as follows:

f represents the calculation of a penalty function value for an optimized parameter vector x of the function f, IMG goes through pieces of X-radiographic information, i.e. individual images, MRK goes through position markers looked up by an automatic identification method, M is the 2D location in the image plane at a parametric value x for a position marker formed in a model geometry, D is the 2D spot in the image plane for position markers looked up by an automatic identification method, DOF goes through degrees of freedom for directions of motion, the total number of which is 6 (3 rotatory directions+3 translatory directions), W is a weighting coefficient for the degree of freedom in each direction of motion, capital delta is the calculation at a parametric value x for a change of the degree of freedom in a penalized direction of motion.

The weighting coefficients W of a penalty function and the penalized degrees of freedom in directions of motion depend on the position of a patient in the apparatus and the stability of support for a patient in various directions. The best values for weighting coefficients and the most extensive directions of patient movements can be found out experimentally.

Figure 2:
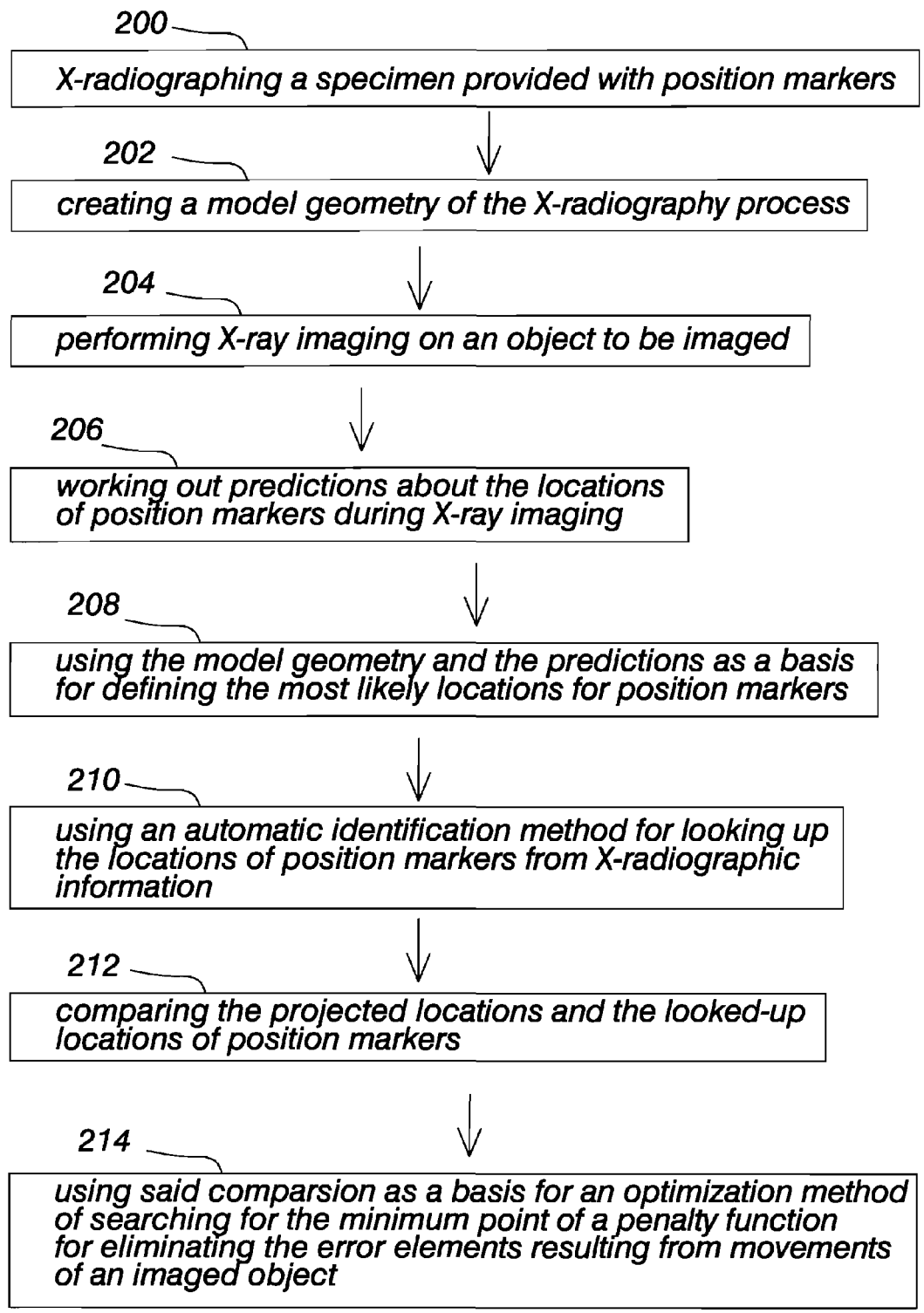
FIG. 2 shows a method of the invention in a procedural block diagram.

FIG. 2 illustrates, in the form of a procedural block diagram, the sequences of a process cycle according to the invention:

a) A first process sequence 200 comprises X-radiographing a specimen provided with position markers.

b) A second process sequence 202 comprises creating a model geography of the X-radiographing process.

c) A third process sequence 204 comprises performing X-ray imaging on an object to be imaged.

d) A fourth process step 206 comprises working out predictions regarding the locations of position markers during X-ray imaging.

e) A fifth process sequence 208 comprises using the model geometry and the predictions as a basis for determining the most likely locations for position markers.

f) A sixth process sequence 210 comprises using an automatic identification method for looking up the locations of position markers from X-radiographic information.

g) A seventh process sequence 212 comprises comparing the projected locations and the looked-up locations of position markers.

h) An eighth process sequence 214 comprises using said comparison as a basis for an optimization method of searching for the minimum point of a penalty function for eliminating error elements resulting from movements of an imaged object.

When the process cycle is completed once, there is no further need for predictions worked out in the process step 206, but as early as in the second process cycle of the method it will be possible to make use of the 3D information compiled in the first process cycle about the imaging process of a patient, such information regarding the disposition of one or more position markers in a set of 3D coordinates graded for an X-ray imaging apparatus.

A method of the invention can be utilized in a wide range of medical X-ray imaging equipment, wherein error elements are caused in X-radiographic information by patient movements during the course of X-radiography. As imaging instruments, the X-ray imaging device comprises an X-ray source for generating X-radiation and a detector for receiving X-radiation, thereby providing X-radiographic information.

An X-ray imaging apparatus according to the invention comprises not only an X-ray imaging device but also a computer unit, the X-radiographic information imaged by means of the X-ray imaging device being transferred thereto either along wires or in a wireless manner. The computer unit comprises means for implementing process steps of the invention. Such means are for example processor-based software implementations. The computer Unit may be located in the immediate proximity of the X-ray imaging device or be distanced even by long communication links from the X-ray imaging device.

Technical implementations more detailed than those described above have not been presented, because in terms of hardware engineering, electronics, and program designing, those can be provided by implementations of the prior art.

Although the invention has been presented in reference to the attached figures and specification, the invention is by no means limited to those as the invention is subject to variations within the scope allowed for by the claims.

The invention claimed is:

1. A method for eliminating error elements caused by movements of an imaged object in X-radiography, said method comprising performing X-radiography on an imaged object for compiling X-radiographic information, characterized in that a model geometry is created of an X-ray imaging process, said creation work comprising a determination of the location for two or more position markers in a set of coordinates graded for an X-ray imaging apparatus, when X-radiography of an imaged object is completed, predictions are worked out regarding the locations of position markers during the imaging session, the locations and predictions determined on the basis of the model geometry are used as a basis for defining projected or most likely locations for the position markers, an automatic position markers identification method is applied for finding the locations of position markers from within a search area in the X-radiographic information, and when the locations of at least two position markers have been found with the automatic position markers identification method, an adjustment of offsets is performed between the projected locations of position markers and the locations of position markers looked up by the automatic identification method for eliminating the error elements resulting from movements of an imaged object.

2. A method as set forth in claim 1, characterized in that an adjustment of of offsets is performed by searching for a minimum point of a function.

3. A method as set forth in claim 2, characterized in that an optimization method is applied in the process of searching for the minimum point of a function.

4. A method as set forth in claim 2, characterized in that the employed function is a penalty function.

5. A method as set forth in claim 1, characterized in that the model geometry is created by X-radiographing a specimen provided with position markers.

6. A method as set forth in claim 1, characterized in that the size of a search area in X-radiographic information is changed by an optimization method.

7. A method as set forth in claim 1, characterized in that, as a first term, the penalty function comprises a root-mean sum of the locations of projected position markers and the locations of position markers determined by the automatic identification method.

8. A method as set forth in claim 1, characterized in that offsets between the locations of projected position markers and the locations of position markers determined by the automatic identification method are determined, a root-square sum being calculated therefor for use as a second term of the penalty function.

9. An X-ray imaging apparatus for eliminating error elements resulting from movements of an imaged object in X-radiography, comprising imaging means for performing X-radiography on an imaged object for compiling X-radiographic information, characterized in that the X-ray imaging apparatus comprises:
   means for creating a model geometry of an X-ray imaging process, said creation work comprising a determination of the location for two or more position markers in a set of coordinates graded for the X-ray imaging apparatus,
   means for working out predictions regarding the locations of position markers during X-radiography,
   means for defining projected or most likely locations for position markers on the basis of determined locations and predictions based on the model geography,
   means for applying an automatic position markers identification method for finding the locations of position markers from within a search area in the X-radiographic information,
   and the X-ray imaging apparatus comprises means for eliminating the error elements resulting from movements of an imaged object, such that when the locations of at least two position markers have been found with the automatic position markers identification method, an adjustment of offsets between the projected locations of position markers and the locations of position markers looked up by the automatic identification method is performed.

10. An X-ray imaging apparatus as set forth in claim 9, characterized in that the X-ray imaging apparatus comprises means for performing an adjustment of offsets by searching for a minimum point of a function.

11. An X-ray imaging apparatus as set forth in claim 10, characterized in that the X-ray imaging apparatus comprises means for applying an optimization method in the process of searching for the minimum point of a function.

12. An X-ray imaging apparatus as set forth in claim 10, characterized in that the X-ray imaging apparatus comprises means for utilizing a penalty function as the function employed in the method.

13. An X-ray imaging apparatus as set forth in claim 9, characterized in that the X-ray imaging apparatus comprises a specimen for creating a model geometry, said specimen being provided with position markers.

14. An X-ray imaging apparatus as set forth in claim 9, characterized in that the X-ray imaging apparatus comprises means capable of using an optimization method for changing the size of a search area in X-radiographic information.

15. An X-ray imaging apparatus as set forth in claim 9, characterized in that the X-ray imaging apparatus comprises means capable of utilizing a penalty function which comprises, as a first term, a root-mean sum of the locations of projected position markers and the locations of position markers determined by the automatic identification method.

16. An X-ray imaging apparatus as set forth in claim 9, characterized in that the X-ray imaging apparatus comprises means for utilizing a penalty function in such a way that offsets between the locations of projected position markers and the locations of position markers determined by the automatic identification method are determined, a root-square sum being calculated therefor for use as a second term of the penalty function.

* * * * *